United States Patent [19]

Malicki et al.

[11] Patent Number: 4,918,375
[45] Date of Patent: Apr. 17, 1990

[54] REFLECTOMETRIC MOISTURE METER FOR CAPILLARY-POROUS MATERIALS, ESPECIALLY FOR THE SOIL

[75] Inventors: Marek Malicki; Wojciech Skierucha, both of Lublin, Poland

[73] Assignee: Polska Akademia Nauk Instytut Agrofizyki, Doswiadczalna, Poland

[21] Appl. No.: 210,662

[22] Filed: Jun. 21, 1988

[30] Foreign Application Priority Data

Jul. 3, 1987 [PL] Poland ................................. 266617
Jul. 3, 1987 [PL] Poland ................................. 266616
Apr. 28, 1988 [PL] Poland ................................. 272128

[51] Int. Cl.⁴ .......................................... G01R 27/28
[52] U.S. Cl. ........................................ 324/642; 73/73; 324/663; 340/604
[58] Field of Search ........... 324/58 B, 58.5 R, 58.5 B, 324/58 R, 61 R; 73/73; 340/603, 604

[56] References Cited

U.S. PATENT DOCUMENTS 4,281,285  7/1981  Bastida ........................... 324/58.5 B
4,396,062  8/1983  Iskander ......................... 324/58.5 B

FOREIGN PATENT DOCUMENTS 1337746  9/1987  U.S.S.R. ........................ 324/58.5 B

OTHER PUBLICATIONS

Measurement of soil content-TOPP, G.C. Soil Sci. Soc. Am. J. Vol. 49, 1985.
Instrument for Reflectomery Analysis of Moisture in Soil-Brochure, 6000 Model Irams, Soil Moisture Equipment Corp. 1985.

Primary Examiner—Reinhard J. Eisenzopf
Assistant Examiner—Robert W. Mueller
Attorney, Agent, or Firm—Ladas & Parry

[57] ABSTRACT

A meter is disclosed for measuring water content, particularly of soil. The probe (1) of the measuring device, fed with the needle electric pulse, is constituted of a set of waveguides connected parallely in the embranchment (2) with the microprocessor controller (10) of the electronic assemblies of the measuring device. Waveguides of the probe are installed in chosen layers of the material studied. The directly measured quantity is the sequence of time periods separating subsequent reflections of the electromagnetic wave propagating in the probe from the particular probe impedance discontinuities. The electromagnetic wave propagation velocity in a chosen layer of the medium is calculated on this basis, and therefrom the dielectric constant of the medium, and finally its moisture content upon which the dielectric constant depends.

21 Claims, 1 Drawing Sheet

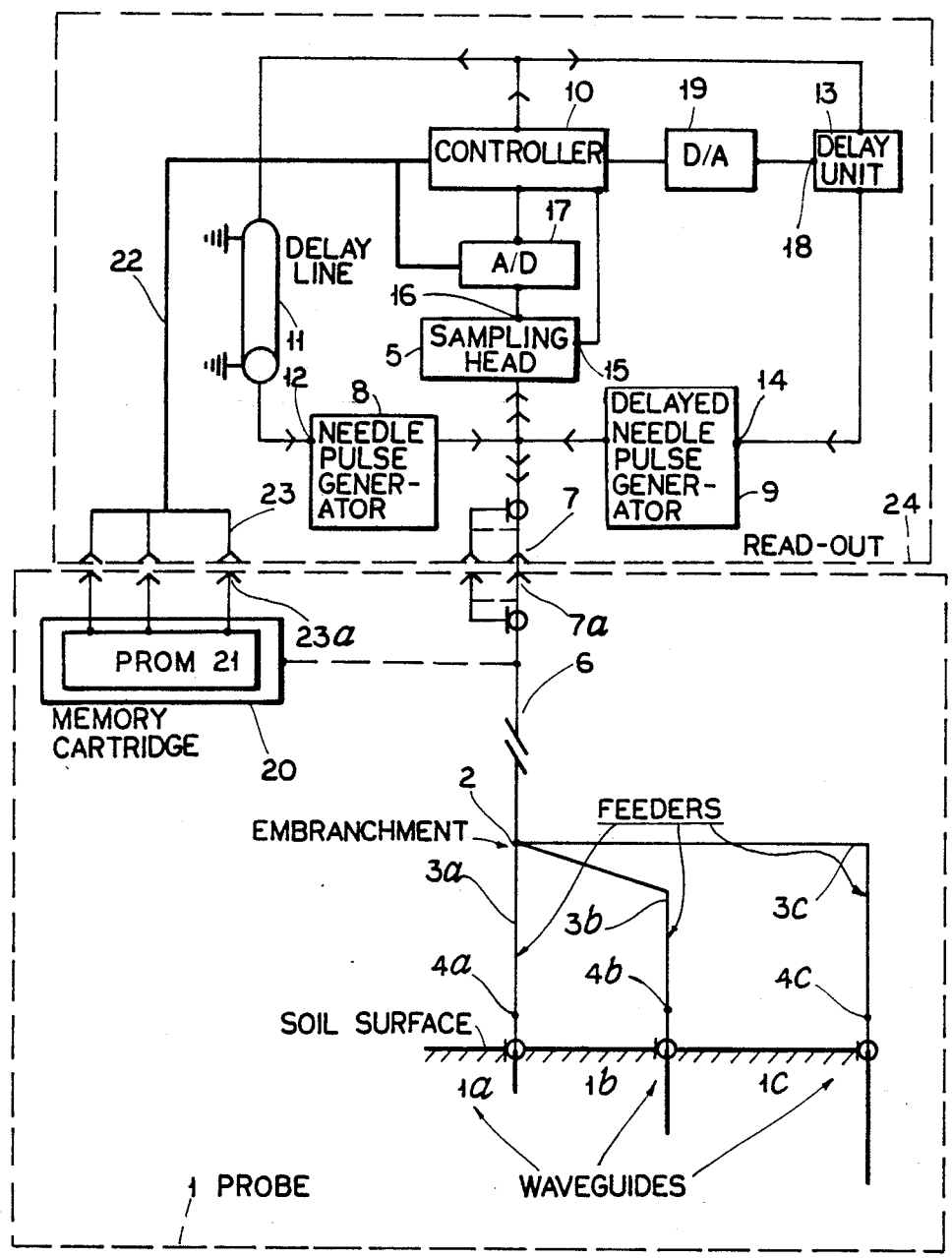

REFLECTOMETRIC MOISTURE METER FOR CAPILLARY-POROUS MATERIALS, ESPECIALLY FOR THE SOIL

The subject of the invention is a reflectometric moisture meter for capillary-porous materials, especially for the soil, which measures the volumetric water content (mass of water in a cubic centimeter of a material), on the basis of the relationship between the dielectric constant of the material and its moisture.

There are known, so called, electrocapacitive-type moisture meters for capillary-porous materials, based on the relationship between dielectric constant of the material and its moisture, whose application allows calculation of moisture on the basis of the relative changes of the capacitance of a condenser-like probe, after it has been filled with the tested material. Because the dielectric constant of pure water (in room temperature) is 81 and because dielectric constant of solid matter, especially of the soil, does not exceed 5, therefore each variation in the material moisture is accompanied by a distinct variation in its resultant dielectric constant. The technical aspect of the moisture measurement, as derived from dielectric constant of the capillary-porous material, especially of the soil, reduces to determination of the material's dielectric constant.

The principal disadvantage of the electrocapacitive meters is the substantial influence of electrochemical polarization on the relation between electrical capacitance of the probe and the moisture of tested material, especially of the soil. This polarization causes that the salinity of the material, in particular of the soil, its temperature, chemical properties of the moistening solution (its acidity and composition), as well as the condition of electrodes (impurities on their surfaces, mechanical stresses) substantially influence the results. Application of high frequency voltage of current supplying the probe leads to decrease of the influence of polarization, on the other hand however, with the frequency increase, technical troubles, resulting from arising parasitic influence of stray inductance and capacitance of the probe, increase too. Therefore alternating voltage applied to excite the electrocapacitive probes is, in most implementations, limited to 0.1–100 MHz frequency range, which does not ensure that the measurements be completely free from the influence of electrochemical polarization. Consequently, the application of the electrocapacitive moisture meters, especially for the soil, needs frequent calibration of the meter, individual for each probe, for each soil type, as well as for each separate probe location in the soil profile.

There exists another method of determining the dielectric properties of materials, where dielectric constant is derived from the measurement of the velocity of electromagnetic wave propagation in the tested material. This method, as giving results free of the error caused by electrochemical polarization, is more suitable for application to moist capillary-porous materials, especially to the soil. One of these methods is the reflectometric method.

The reflectometric method of the dielectric constant determination is based on the measurement of the velocity of electromagnetic wave propagation in a material as related to its dielectric constant. The respective relationship, for non-magnetic materials having low dielectric loss, can be simplified to:

$$V = \frac{c}{\sqrt{K}}$$

where:
- V—electromagnetic wave propagation velocity in a material,
- c—electromagnetic wave (light) propagation velocity in vacuum,
- K—relative dielectric constant of the material.

A section of a waveguide is inserted into the soil in order to measure its moisture. The waveguide may be of any type and shape. It ought to have air as the dielectric and can be opened or shortcircuited at its end. The waveguide input is connected to a pulse generator by a transmission line (a coaxial or a flat, balanced cable), thereinafter referred to as the feeder. A voltage pulse, introduced from the generator to the feeder, causes electromagnetic wave to develop in the feeder. This wave propagates along the feeder towards the waveguide inserted in the soil, reaches its input and continues to propagate, in the soil, towards the waveguide end, partly radiating its energy into the soil. At the feeder-waveguide junction there is an impedance discontinuity interposed (impedance of feeder differs from the waveguide impedance). It causes partial reflection of the pulse energy which returns towards the pulse generator. The remaining pulse energy propagates in the soil, reflects again from the waveguide end, and returns towards the pulse generator as well. By measuring time separating the said reflections and accounting for the waveguide length it is possible to derive velocity of the wave propagation in the material (soil), and then, according to the formula mentioned, its dielectric constant, and finally—the related soil moisture.

It is to be emphasized that a single soil moisture measurement (i.e. the measurement concerning a single layer of the soil whose thickness is determined by the waveguide length), is, in general, useless. Measurements of the soil moisture are, in most cases, needed for the determination of water content distribution in the soil profile. The moisture profile is obtained by determining the vertical water distribution in the soil, on the basis of quasi-simultaneous measurements of the soil moisture in several selected depths, from the soil surface, downwards to the parent material of the soil, not deeper, however, than 1.5 m.

Since 1980 the TEKTRONIX cable tester, model 1502, has been applied for the reflectometric measurements of moisture, especially for the soil. It operates with a step pulse (the rapid change of voltage from zero to its maximal value) having 145 ps rise time (G. C. Topp and J. L. Davis, Measurement of Soil Water Content using Time-domain Reflectometry (TDR): A Field Evaluation. Soil Sci. Soc. Am. J., vol. 49, 1985,: 19–24). This tester is designed for the faults in transmission lines location as well as for the determination of the fault impedance type (break, leakage with the impedance having an active or passive predominant component, etc.).

In 1984 the Canadian firm, FOUNDATION INSTRUMENTS INC., offered IRAMS (Instrument for Reflectometry Analysis of Moisture in Soil), the device designed exclusively for the soil moisture measurement, now produced by SOIL MOISTURE EQUIPMENT CORP., P.O. Box 30025, Santa Barbara, CA 93105, USA.

The actually applied probe, used in combination with the said TEKTRONIX 1502 cable tester as well as with the said IRAMS measuring device, is composed of a section of a feeder ended with an open-ended waveguide which consists of two parallel metal rods of circular cross-section and which is inserted into the soil profile (G. C. Topp and J. L. Davis, Measurement of Soil Water Content using Time-domain Reflectometry (TDR): A Field Evaluation. Soil Sci. Soc. Am. J., vol. 49, 1985,: 19-24). With the application of such a probe it is possible to make measurements concerning a single layer of the soil. There are known attempts of measuring moisture in several layers of the soil simultaneously. A single probe equipped with a waveguide similar to the said one is applied, composed of rods whose diameter changes stepwise within sections, each section of the length of several cms, thereinafter referred to as the notch. There are several notches along the waveguide, separated by a certain distance, the same for both rods (G. C. Topp and J. L. Davis, Measurement of Soil Water Content using Time-domain Reflectometry (TDR): A Field Evaluation. Soil Sci. Soc. Am. J., vol. 49, 1985,: 19-24). Because of impedance discontinuities at the notches, the pulse energy is reflected partly from each of them, marking subsequent layers of the soil through which the electromagnetic wave has been propagated. The measurement of periods of time separating successive reflections makes it possible to determine the soil moisture profile, according to the said procedure.

The disadvantage of the cable tester in its applications for moisture measurement of capillary-porous materials, especially of the soil, is the stepwise shape of the operating pulse as well as the way the probe response to this pulse is monitored. The probe response to this pulse is read from the synchroscope (sampling oscilloscope) screen or from an X-Y recorder, the said tester is provided with, which is troublesome in interpretation and may lead to considerable errors. The fact that the original purpose of the device was not moisture measurement as well as its considerable electric power rating make it unsuitable for applications with battery operated, automatic data logging systems.

The authors of the invention know no technical details of the said IRAMS reflectometric moisture meter design. From the lecture of its characteristics it can be concluded that the meter is not applicable for the automatic irrigation systems control as well as for the soil moisture logging because the said IRAMS is operated manually. A user has to switch over the probes by successive manual operations, consisting in disconnection of one and connection of another probe to the instrument input, each time inscribing the individual length of a particular probe waveguide into the IRAMS device.

Attempts are known at switching the probes over using the microwave switches having impedance matching the one of the feeder (which raises the price of the moisture measuring system and complicates its installation). A special switching box used to be available from the said IRAMS. The MOISTURE EQUIPMENT CORP. does not offer any switch for waveguide-type probes.

The disadvantage of the said notched probe consists in relatively large pulse energy loss at the notches (which, in many cases, makes the pulse reflected from the deeper part of the waveguide unreadable) as well as remarkable weakness of the mechanical strength of the probe.

The purpose of the invention was to design a moisture meter for capillary-porous media, capable to work automatically in different, user programmable modes, especially in the mode of automatic control of irrigation systems as well as in the soil moisture dynamics logging mode, where the soil moisture measurement would be performed at many selected depths of the soil profile without the necessity of switching over the particular probes installed at these depths and during each measurement compensation for the meter drift as well as inscription of parameters of the actually active probe would be executed automatically. This purpose has been achieved as described below.

The reflectometric moisture meter of the invention includes a probe composed of n waveguides, where $n=1, 2, \ldots, N$. These waveguides can be of any kind and shape and they ought to have air as dielectric. The waveguides can be of equal or different lengths and their ends can be opened or shortcircuited. The waveguides are connected in parallel in an embranchment by transmission line sections, thereinafter referred to as feeders. Each particular waveguide-feeder system is connected by an input connector to the meter sampling head, by a section of common feeder. Each of the feeders, connecting particular waveguides to the embranchment, is provided with a local, stepwise discontinuity of its impedance, thereinafter referred to as the time marker, interposed in a feeder by partial, purposefully introduced disturbance of its properties.

Needle pulses from a needle pulse generator and a delayed needle pulse generator are introduced to an input connector and to the sampling head. These parameters are triggered by pulses from a controller. One of the controller outputs is appropriately connected to the needle pulse generator input and, by the adjustable delay unit, to the input of the delayed needle pulse generator. Another controller output is led to the sampling head reset input. Output of the sampling head is then inputted to a voltage reading device.

A typical microprocessor-driven controlling unit is applied as the said controller. It consists of: a microprocessor, a nonvolatile programmable read only memory, thereinafter referred to as PROM, a random access memory, thereinafter referred to as RAM, a display and a keyboard. The keyboard helps to program the device in different modes of action: an automatic moisture logging mode, a meter—peripheral device (a tape recorder, a disk drive, a computer) data transfer mode or an automatic irrigation system control mode. The microprocessor-driven controlling unit, thereinafter referred to as the controller, coordinates the sampling head and both the needle pulse generators interaction, according to the program stored in the said PROM and—if working in the moisture logging mode—saves the measured moistures in the said RAM, assigning to each of them the respective depth, day and hour as well.

The triggering input of the needle pulse generator is connected to the controller by a delay line section, whereas the delayed needle pulse generator triggering input is connected to the controller by the voltage controlled delay unit. The delay unit's delay controlling input is connected to the controller by a digital-to-analog converter. The sampling head output is connected to the controller by the voltage reading device, constituting an analog-to-digital converter.

There is a multiple pin terminal (jack or plug) inseparably attached to the probe, which contains a nonvolatile programmable read only memory integrated circuit, of PROM, EPROM, EEPROM or similar type. Its pins are electrically connected to the terminal pins. The terminal pins are connected to the controller bus by another terminal (plug or jack) which is complementary to the said multiple pin terminal.

The waveguides constituting the probe may be of equal or different lengths. Periods of time during which reflections related to a particular feeder-waveguide occur, thereinafter referred to as time windows, cannot overlap one with another. Therefore the length of feeders, connecting particular waveguides to the embranchment, differ in order to assure the appropriate, introduced by the feeders residual delays, time separation of the said time windows. These lengths are determined by the pulse propagation times between the embranchment and the markers as follows:

$$t_{(L_{n+1})} \geq t_{(L_n)} + t_d + 18 \frac{l_n}{c}$$

and:

$$t_{(L_N)} + t_d + 18 \frac{l_N}{c} \leq 2 t_{(L_1)}$$

where:
$t_{(L_{n+1})}$—time during which the pulse covers the double embranchment—time marker distance, in the feeder subsequent as to its length,
$t_{(L_n)}$—similarly, for the preceding feeder in the length sequence,
$t_{(L_n)}$—time during which the pulse covers the double embranchment—marker distance, in the last feeder in the length sequence,
$t_{(L_1)}$—similarly, for the first feeder in the length sequence,
$l_n$—length of the preceding waveguide in the length sequence,
$l_N$—length of the last waveguide in the length sequence,
$t_d$—dead time equal to $(t_{in} - t_1)$, where $t_{in}$ is the instant in which the pulse is reflected from the feeder—waveguide junction and $t_1$ is the instant in which the pulse is reflected from the time marker,
c—velocity of light in vacuum.

$$18 \frac{l_n}{c}$$

time during which the pulse covers the distance of double length of the feeder $l_n$, when completely immersed in water.

Assuming arbitrarily the shortest feeder length and computing the respective time of the pulse propagation:

$$t_{(L_1)} = \frac{2 L_1}{c} \sqrt{K}$$

where $K \approx 2.5$ is relative dielectric constant of the feeder insulating substance, one can derive the second (in the length sequence) feeder length, according to the formula determining the $t_{(L_{n+1})}$.

Analogously, knowing the second feeder length it is possible to derive the length of the third one and so on. The $t_{(L_N)}$ determining formula imposes the limitation coming from multifold appearance of the reflections in the feeder—waveguide system. The earliest reflection of the second order, originating from the shortest system, cannot appear earlier than the latest reflection of the first order.

The reflectometric moisture meter of the invention is free of disadvantages, characteristic for the cable tester, arising from the application of the step pulse and from monitoring of the probe response with a cathode ray tube oscilloscope screen or an X-Y recorder. The moisture meter of the invention operates with a $\sin^2$-like needle pulse and monitors the probe response with the application of the said typical microprocessor-driven controller which controls the collaboration of the meter sub-assemblies as well as processes the data, including storage of the results. Such a solution of the meter design makes it possible to apply it in different, user programmable, modes—in particular—in the mode of the irrigation systems control and in the mode of the automatic logging of moisture dynamics, especially of the soil.

The appropriate differentiation of feeder lengths makes it possible to read simultaneously the moisture in many layers of the soil without application of electrical switches. Number of the layers subject to measurement equals the number of waveguides the probe is provided with. Each of the said markers is located between a feeder ending waveguide and the said embranchment. The presence of the embranchment interposes an impedance discontinuity as well, which creates another time marker common for all feeders constituting the probe. A section of any chosen feeder, embraced by these two markers, constitutes the time standard since properties of the line the feeders are made of are sufficiently stable. This time standard is used during measurement for autocalibration of the meter of the present invention. Such a solution makes it unnecessary to care about considerable drift of the said delay unit, whose elimination requires much trouble and expense as is the case of the TEKTRONIX 1502 cable tester.

If the probe comprises only one waveguide (n=1), then there is an impedance discontinuity introduced instead of the said embranchment as the second time marker.

Application of a PROM or similar type of the nonvolatile, programmable memory in the meter of the present invention, which is inseparably attached to each particular probe and which remains connected to the meter during the measurement, makes it unnecessary to inscribe manually the characteristics of the particular probe into the meter controlling software each time the measurement is to be executed as is the case of IRAMS with regard to particular waveguide lengths. In the case of the meter of the present invention there are other specific parameters of the probe stored in the PROM besides the length of the applied waveguide, such as: time standard and dead time as well as parts of specific for the waveguide shape and application software. Such a solution makes the meter of the present invention unrestrictedly flexible, providing a user with a broad variety of application fields.

The sole FIGURE shows the structure of the meter of the present invention.

The meter probe 1 constitutes the assembly of three waveguides 1a, 1b, 1c, each composed of a pair of oblong dagger-like electrodes, perpendicular to each another. The lengths of these pairs successively increase for each particular waveguide. In the said embodiment the lengths of the waveguides 1a, 1b, 1c, are respectively: 0.1, 0.25 and 0.50 m. These waveguides are interconnected in parallel at the embranchment 2 by transmission lines 3a, 3b, 3c, thereafter referred to as feeders, equal in their specific impedance but differing as to their lengths. In the embodiment shown the lengths of the feeders 3a, 3b, 3c are respectively: 9, 10 and 12 mts, whereas the impedance of each of them is 50 ohm. Each feeder possesses a local stepwise impedance discontinuity 4a, 4b, 4c, thereafter referred to as time marker, interposed between a particular waveguide 1a, 1b, 1c input and the embranchment 2. The embranchment 2 is connected to the sampling head 5 by the section of the common feeder 6, whose length in the said embodiment is 15 mts.

Needle pulses from the needle pulse generator 8 and the delayed needle pulse generator 9 are connected to the input connector 7 and to the sampling head 5. These generators are triggered by pulses from the controller 10. One of the controller 10 outputs is connected to input 12 of the needle pulse generator 8 by the delay line 11 and, through the adjustable delay unit 13, to the input 14 of the delayed needle pulse generator 9. Another controller 10 output is connected to the sampling head 5 reset input 15. The output 16 of the said sampling head is connected to the voltage reading device 17, constituting an analog-to-digital converter.

A microprocessor-driven controller, referred to as controller 10, is applied in the meter of the invention. It coordinates the interaction of the sampling head 5 and both the needle pulse generators 8 and 9. The needle pulse generator 8 triggering input 12 is connected to the controller 10 by the delay line section 11, which appropriately matches residual delays introduced by lines connecting both the needle pulse generators 8, 9 with the controller 10. The delay unit's 13 delay controlling input 18 is connected to the controller 10 by the digital-to-analog converter 19. The output 15 of the sampling head 5 is connected to the controller 10 by the analog-to-digital converter 17.

There is a terminal 20 inseparably attached to the probe 1, which contains a nonvolatile programmable read only memory integrated circuit 21 of PROM, EPROM, EEPROM or similar type, with pins electrically connected to the terminal 20 pins. The pins of the terminal 20 are connected to the controller bus 22 by the terminal 23 which is complementary to the said terminal 20.

The value which is measured directly is the time period during which the electromagnetic wave covers the distance along the double length from the feeder embranchment to the time marker section as well as from the marker to the waveguide end section. On the basis of these measurements the controller 10 computes under control of a resident program the corrections for the device drift and then the material (soil) dielectric constant and finally—its moisture.

Pulses from the controller 10, of frequency order of 1 kHz, synchronize the interaction of the sampling head 5 and the pulse generators 8, 9, which produce the needle pulses having the rise and the fall time of order of 100 ps. Such fast and narrow pulses (during 100 ps light in vacuum covers the distance of 3.3 cm) cannot be processed in real time for the lack of sufficiently fast, active, electronic devices. For this reason the well known sampling technique is applied here which is widely applied in the sampling oscilloscopes for observation of extremely fast electrical pulses. It consists in sampling and storing of the tested run voltage samples, sampled at different instants. The run is repeated as many times as the number of samples to be collected. These samples are then retrieved in the same order as they were collected, with arbitrarily lower speed however, reproducing this way the single pulse run.

The pulse from the controller 10 resets the sampling head 5 memory and triggers both needle pulse generators 8, 9. The triggering action of the delayed needle pulse generator 9 is controlled by the delay unit 13. Both pulses feed the probe 1 through the input connector 7 and, independently, cause the development of electromagnetic wave in the feeder 6 which propagates towards the waveguide 1a, 1b, 1c ends, dividing its energy between the said three waveguides and undergoing the mentioned reflections from the probe impedance discontinuities.

Both the incident and the reflected pulses appear at the input of the sampling head 5. The sampling head is insensitive to pulses having voltage lower than a certain threshold voltage, which is set a bit higher than the voltage of the incident pulse. However, as a needle pulse reflected from the probe and the delayed needle pulse superimpose each other, the resulting voltage exceeds the threshold and its sample is taken. A properly biased Schottky diode, as the one having sufficiently short switching time, serves as the gate which allows, or not, taking of the sample. When the gate opens, the voltage captured by the sampling head 5 is directly proportional to the respective instant voltage of the sampled run.

The pulse from the delayed needle pulse generator 9 is shifted in phase (in time) by the delay unit 13 whose delay is controlled by voltage from the digital-to-analog converter 19 set by the controller 10. The pulse delay is directly proportional to the said voltage.

The meter of the present invention can be applied as a measuring and/or controlling device in science and engineering, everywhere where the moisture of a material is to be controlled. It can be applied for any such capillary-porous material which allows introduction of the probe in a nondestructive way. Such materials include: the soil, agricultural products (grain, hop cones, tobacco leaves, hay), food industry products (flour, bakery products), wood, moulding sand, subgrades, building foundations etc.

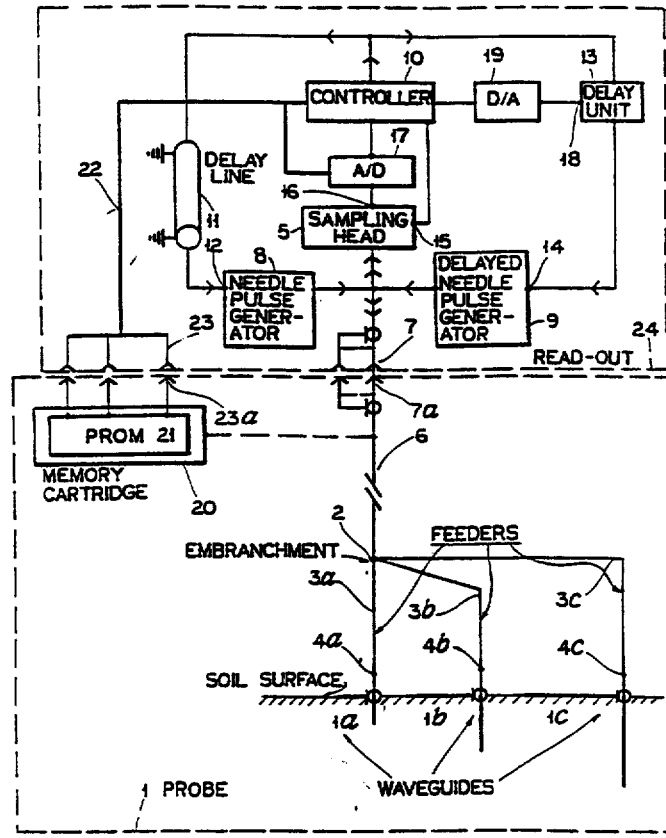

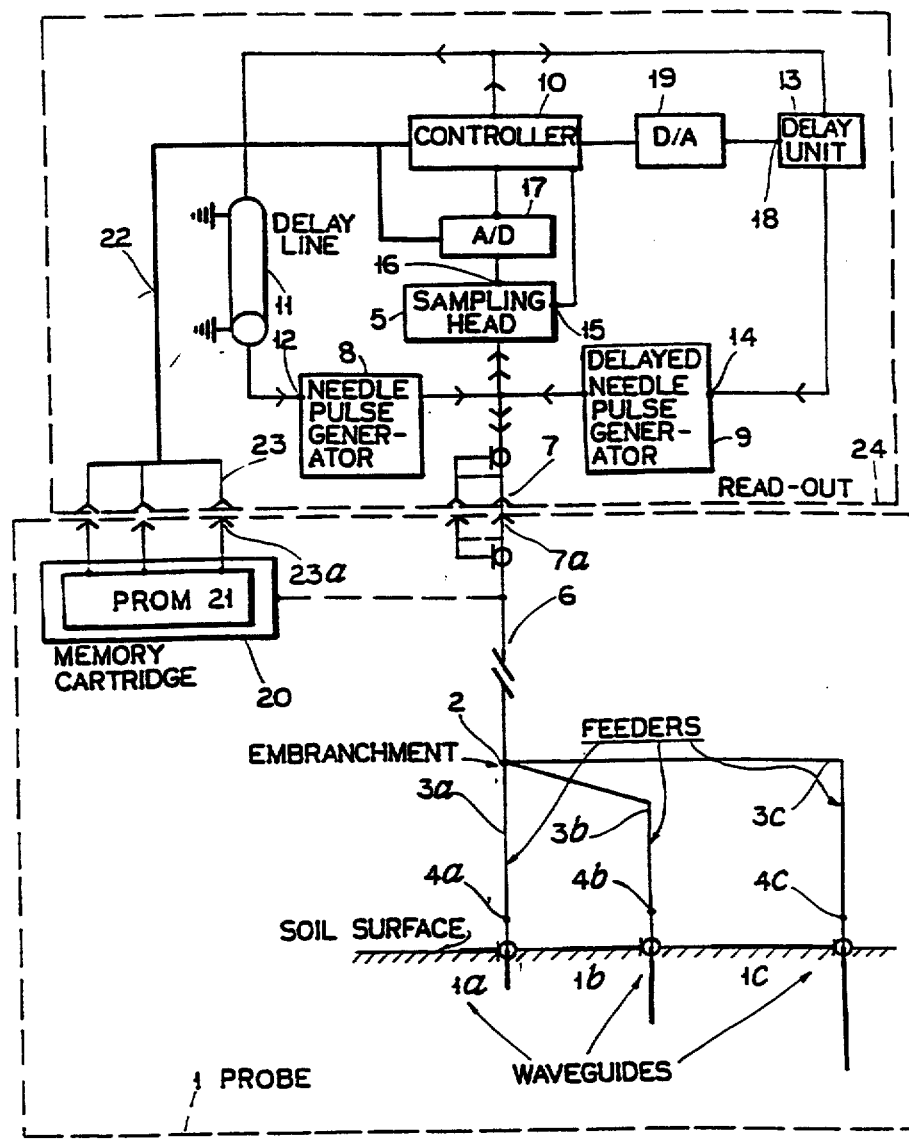

We claim:

1. A reflectometric moisture meter for capillary-porous materials comprising:
   read-out means for reading the moisture of capillary-porous media from probe means installed in media of interest; said probe means measuring the velocity of electromagnetic wave propagation in said medium as determined by its moisture,
   said read-out means further comprising:
   a controller means to control co-operation of components of the read-out means and to compute results of the measurements;
   an interface means for the communication of the controller with out components of said reflectometric moisture meter;
   voltage pulse means to generate two needle pulses of voltage to supply the probe means;
   pulse delay means to set the phase difference between said needle pulses of voltage; and
   sampling means to catch samples of voltage from pulses returning as reflected from the probe means.

2. The reflectometric moisture meter defined in claim 1 wherein the controller means comprises a microprocessor-driven controller means.

3. The reflectometric moisture meter defined in claim 2 wherein the microprocessor-driven controller means further comprises a microprocessor, a programmable read only memory, PROM, a random access memory, RAM, a display and a keyboard.

4. The reflectometric moisture meter defined in claim 1 wherein the interface means further comprises an analog-to-digital converter to write particular samples of voltage into said controller's RAM, a digital-to-analog converter to set the voltage which controls the delay contributed by said pulse delay means, and a contact means to connect said voltage pulse means and said sampling means to the probe means.

5. The reflectometric moisture meter defined in claim 1 wherein the voltage pulse means further comprises two needle pulse voltage generators.

6. The reflectometric moisture meter defined in claim 5 wherein the needle pulse generators are driven by the controller means through the mediation of said pulse delay means.

7. The reflectometric moisture meter defined in claim 1 wherein the pulse delay means comprises further a section of a delay line having fixed delay and a voltage controlled adjustable delay unit.

8. The reflectometric moisture meter defined in claim 7 wherein the voltage controlled adjustable delay unit is driven by the controller means through the mediation of said digital-to-analog converter.

9. The reflectometric moisture meter defined in claim 1 wherein the sampling means further comprises a sampling head controlled by said controller means to catch samples of input voltage incoming from said probe means through the mediation of the contact means and which are further sent to the controller means by the mediation of said analog-to-digital converter.

10. The reflectometric moisture meter defined in claim 4 wherein the contact means further comprises a microwave-type input connector to connect a chosen probe and a multiple pin connector to connect a memory cartridge terminal means which is inseparably attached to this probe.

11. A reflectometric moisture meter for capillary-porous materials comprising:
read-out means for reading the moisture of capillary-porous media from probe means installed in media of interest; said probe means measuring the velocity of electromagnetic wave propagation in said medium as determined by its moisture,
said probe means further comprising:
sensor means to force electromagnetic waves to propagate through said medium,
feeder means to connect said sensor means in-parallel at an embranchment;
main feeder means to link said embranchment with an input connector of said read-out means;
time marker means to provide the probe means with a time reference; and
memory cartridge terminal means to supply characteristics of the probe means actually read.

12. The reflectometric moisture meter defined in claim 11 wherein the sensor means further comprises $n=1, 2, \ldots, N$ waveguides which are introduced into an investigated medium, linked in an embranchment by the mediation as feeder means.

13. The reflectometric moisture meter defined in claim 11 wherein the feeder means further comprises the amount, $n=1, 2, \ldots, N$, of sections of a transmission line equal to the amount of said waveguides.

14. The reflectometric moisture meter defined in claim 11 wherein the main feeder means further comprises a section of a transmission line ended with a complementary connector which is compatible to the connector mentioned in claim 10 to connect said embranchment with said input connector.

15. The reflectometric moisture meter defined in claim 11 wherein the time marker means further comprises an impedance discontinuity means.

16. The reflectometric moisture meter defined in claim 15 wherein the impedance discontinuity means further comprises not less than two, stepwise, local specific impedance discontinuities interposed between each said waveguide and said input connector.

17. The reflectometric moisture meter defined in claim 16 wherein one of the stepwise local specific impedance discontinuities further comprises a small mechanical disturbance purposely installed over a very short section of each of said feeder means, causing its impedance to be locally a bit difference than the specific impedance of the transmission line constituting the feeder means.

18. The reflectometric moisture meter defined in claim 16 wherein another of the stepwise local impedance discontinuities is constituted by said embranchment.

19. The reflectometric moisture meter defined in claim 11 wherein the memory cartridge terminal means further comprises a nonvolatile memory means to store specific characteristics of said probe means, and a contact means to join the nonvolatile memory means to said controller means.

20. The reflectometric moisture meter defined in claim 19 wherein the nonvolatile memory means further comprises a programmable read only memory means.

21. The reflectometric moisture meter defined in claim 19 wherein the contact means further comprises a complementary multiple pin terminal which is compatible to said multiple pin connector mentioned in claim 10.

* * * * *

UNITED STATES PATENT AND TRADEMARK OFFICE
CERTIFICATE OF CORRECTION

PATENT NO. : 4,918,375
DATED : April 17, 1990
INVENTOR(S) : Marek Malicki, et al.

It is certified that error appears in the above-indentified patent and that said Letters Patent is hereby corrected as shown below:

The title page should be deleted to appear as per attached title page.

The sheet of drawing should be deleted to appear as per attached sheet.

Signed and Sealed this

Twelfth Day of September, 1995

Attest:

BRUCE LEHMAN

*Attesting Officer*   *Commissioner of Patents and Trademarks*

United States Patent

Malicki et al.

[11] Patent Number: 4,918,375
[45] Date of Patent: Apr. 17, 1990

[54] REFLECTOMETRIC MOISTURE METER FOR CAPILLARY-POROUS MATERIALS, ESPECIALLY FOR THE SOIL

[75] Inventors: Marek Malicki; Wojciech Skierucha, both of Lublin, Poland

[73] Assignee: Polska Akademia Nauk Instytut Agrofizyki, Doswiadczalna, Poland

[21] Appl. No.: 210,662

[22] Filed: Jun. 21, 1988

[30] Foreign Application Priority Data

Jul. 3, 1987 [PL] Poland ............................. 266617
Jul. 3, 1987 [PL] Poland ............................. 266616
Apr. 28, 1988 [PL] Poland ............................. 272128

[51] Int. Cl.⁴ ............................................. G01R 27/28
[52] U.S. Cl. ................................. 324/642; 73/73; 324/663; 340/604
[58] Field of Search ............ 324/58 B, 58.5 R, 58.5 B, 324/58 R, 61 R; 73/73; 340/603, 604

[56] References Cited

U.S. PATENT DOCUMENTS

4,281,285  7/1981  Bastida ........................ 324/58.5 B
4,396,062  8/1983  Iskander ...................... 324/58.5 B

FOREIGN PATENT DOCUMENTS

1337746  9/1987  U.S.S.R. ........................ 324/58.5 B

OTHER PUBLICATIONS

Measurement of soil content-TOPP, G.C. Soil Sci. Soc. Am. J. Vol. 49, 1985.
Instrument for Reflectomery Analysis of Moisture in Soil-Brochure, 6000 Model Irams, Soil Moisture Equipment Corp. 1985.

*Primary Examiner*—Reinhard J. Eisenzopf
*Assistant Examiner*—Robert W. Mueller
*Attorney, Agent, or Firm*—Ladas & Parry

[57] ABSTRACT

A meter is disclosed for measuring water content, particularly of soil. The probe (1) of the measuring device, fed with the needle electric pulse, is constituted of a set of waveguides connected parallely in the embranchment (2) with the microprocessor controller (10) of the electronic assemblies of the measuring device. Waveguides of the probe are installed in chosen layers of the material studied. The directly measured quantity is the sequence of time periods separating subsequent reflections of the electromagnetic wave propagating in the probe from the particular probe impedance discontinuities. The electromagnetic wave propagation velocity in a chosen layer of the medium is calculated on this basis, and therefrom the dielectric constant of the medium, and finally its moisture content upon which the dielectric constant depends.

21 Claims, 1 Drawing Sheet